United States Patent

Okada et al.

[11] Patent Number: 5,334,305
[45] Date of Patent: Aug. 2, 1994

[54] REFERENCE ELECTRODE

[75] Inventors: Kohji Okada, Iwakura; Minato Ando, Aichi; Jun-ichi Tokumoto, Konan; Takashi Katoh, Kasugai, all of Japan

[73] Assignee: NGK Spark Plug Co., Ltd., Aichi, Japan

[21] Appl. No.: 911,584

[22] Filed: Jul. 10, 1992

[30] Foreign Application Priority Data

Jul. 10, 1991 [JP] Japan .................. 3-195096

[51] Int. Cl.$^5$ ............................................ G01N 27/30
[52] U.S. Cl. .................................... 204/435; 204/416
[58] Field of Search ........................ 204/416–420, 204/435

[56] References Cited

U.S. PATENT DOCUMENTS

| | | | |
|---|---|---|---|
| 3,103,480 | 9/1963 | Watanabe et al. | 204/420 |
| 3,455,793 | 7/1969 | Watanabe et al. | 204/435 |
| 3,833,495 | 9/1974 | Grubb | 204/435 |
| 4,390,406 | 6/1983 | Kato et al. | 204/435 |
| 5,066,383 | 11/1991 | Yamaguchi et al. | 204/435 |

FOREIGN PATENT DOCUMENTS 62-47546 3/1987 Japan .

OTHER PUBLICATIONS

Orion Research Inc. Newsletter/Specific Electrode Technology, vol. 1, No. 4, Sep. 1969, pp. 21-23.
Burrows et al. J. Electrochem. Soc.: Electrochemical Science, Apr. 1968, pp. 365-367.

*Primary Examiner*—T. Tung
*Attorney, Agent, or Firm*—Fish & Richardson

[57] ABSTRACT

An internal liquid for a reference electrode containing lithium chloride (LiCl) and ammonium nitrate (NH$_4$NO$_3$) in a dissolved state at a ratio [NH$_4$NO$_3$]/[LiCl]≧4. Internal liquid also contains AgCl to saturation for use with an Ag—AgCl internal electrode, and is in a gellated state or impregnated in a highly water-absorbent synthetic resin. It is used in conjunction with a comparison electrode or an internal reference electrode for an ion-selective electrode.

Drying up of the internal liquid in the gellated state is minimized so that the function of the internal liquid as a liquid bridge may be displayed for a prolonged period of time. If the ionic concentration of the liquid under examination is changed, liquid potential difference remains substantially unchanged to provide a stable reference electrical potential.

9 Claims, 2 Drawing Sheets

REFERENCE ELECTRODE

BACKGROUND

1. Field of the Invention

This invention relates to an electrode which will give a reference electrical potential for a system for potentiometrically measuring an ion concentration in a solution. More particularly, it relates to an electrode which may be used as a reference (control) electrode or as an internal reference electrode of an ion electrode (ion-selective electrode). The ion electrode includes, for example, a glass electrode used for pH measurements.

In the present specification, the reference (control) electrode and the internal reference electrode of the ion electrode are termed collectively as the "reference electrode".

2. Related Art and Discussion Thereof

As a reference (control) electrode, a silver-silver chloride electrode is used extensively. A potassium chloride solution, saturated with silver chloride, is usually employed as an internal liquid, in which a silver-silver chloride internal electrode is immersed. Occasionally, the internal liquid is communicated with a liquid under examination by means of a salt bridge solution (refer to page 45 of "Ion Denkyoku to Kouso Denkyoku" (Ion Electrode and Enzymatic Electrode) by Shuichi Suzuki).

However, if the internal liquid is present in the state of solution, it may be depleted due to drying or the like. Thus it becomes necessary to replenish the internal liquid for prolonged use. Although it has been attempted to gellate the internal liquid, the gel is similarly deprived of moisture due to drying on prolonged storage so that it no longer acts as a liquid bridge. Therefore, there is much to be required in the conventional reference electrodes.

SUMMARY OF THE DISCLOSURE

Accordingly it is an object of the present invention to provide a novel reference electrode which is free from the drawbacks aforementioned.

Further objects will become apparent in the entire disclosure.

The reference electrode of the present invention is characterized in that it contains, as an internal liquid, lithium chloride (LiCl) and ammonium nitrate ($NH_4NO_3$) in a dissolved state. In this case, the concentrations in the internal liquid of lithium chloride and ammonium nitrate are such that the transport numbers of $NH_4^+$ ions and $NO_3^-$ ions of 0.5/0.5 become predominant. Thus the $NH_4NO_3$/LiCl concentration ratio is adjusted, inter alia, to [$NH_4NO_3$]/[LiCl]$\geq$4.

Since lithium chloride and ammonium nitrate, which are highly hygroscopic salts of inorganic electrolytes, are contained in the internal liquid of the electrode of the present invention, in place of potassium choloride (KCl) the internal liquid may be prevented from being dried.

Since the internal liquid for the reference electrode of the present invention contains an electrolyte showing high hygroscopicity, it is possible to prevent the internal liquid from being dried up. Above all, if the internal liquid is in the gellated state, it is possible to sufficiently prevent the gel from being dried up such that the internal liquid may continue to play the role of a liquid bridge even on storage at room temperature for a prolonged period of time. Besides, since the electrolyte in the internal liquid in the gellated state is composed mainly of $NH_4^+$ ions and $NO_3^-$ ions showing substantially the same ionic mobility, there are scarcely fluctuations in the liquid potential difference between the liquid under examination and the internal liquid acting as a liquid bridge, so that a constant reference potential may be produced.

DESCRIPTION OF THE PREFERRED EMBODIMENTS

Above all, when the internal liquid is gellated, the gel surface is scarcely dried but is maintained at all times in a wet state, even on prolonged storage in a chamber. In this manner, the function of the internal liquid as a liquid bridge may be maintained stably for a prolonged period of time. On the other hand, since the electrolyte in the internal liquid is mainly composed of $NH_4^+$ ions and $NO_3^{31}$ ions showing substantially the same values of ionic mobility, there are substantially no fluctuations in the liquid potential difference between the liquid under examination and the internal liquid. As the result, a stable reference electrical potential may be achieved.

$NH_4^+$ ions and $NO_3^-$ ions of ammonium nitrate are substantially equivalent in the ionic mobility, whereas $Li^+$ ions and $Cl^-$ ions of lithium chloride differ significantly in the ionic mobility. Therefore, by setting the concentration of ammonium nitrate [$NH_4NO_3$] so as to be higher than the concentration of lithium chloride [LiCl], it becomes possible to render the transport numbers of cations and anions in the internal liquid substantially equal to each other so that the internal liquid may function appropriately as a liquid bridge, above all, as an internal liquid, of a reference electrode exhibiting a constant electrical potential without dependency on changes in the ionic concentration in the liquid under examination.

On the other hand, a silver-silver chloride (Ag—AgCl) electrode, which is an ordinary internal electrode, is in need of a chloride salt for maintaining a constant oxidation/reduction potential. As such chloride salt, LiCl, which also shows a high hygroscopicity, gives particularly desirable results. From these viewpoints, the LiCl concentration [LiCl] is adjusted to 0.1 mol·dm$^{-3}$$\leq$[LiCl]$\leq$1 mol·dm$^{-3}$ and preferably to about 0.5 mol·dm$^{-3}$, whereas the concentration ratio [$NH_4NO_3$]/[LiCl] is adjusted to 4 to 8, preferably to 5 to 7 and more preferably to about 6.

The concentration of ammonium nitrate [$NH_4NO_3$] is set based on such concentration of lithium chloride [LiCl] and the above-mentioned concentration ratio. Usually, the concentration of ammonium nitrate [$NH_4NO_3$] is set to [$NH_4NO_3$]$\leq$8 mol·dm$^{-3}$. Above all, if the internal liquid is to be gellated and such gellation is to be facilitated, the concentration of ammonium nitrate [$NH_4NO_3$] is preferably set to [$NH_4NO_3$]$\leq$4 mol·dm$^{-3}$. Meanwhile, if LiCl is added solely or at a concentration higher than that of ammonium nitrate, the transport numbers of the $Li^+$ ions and $Cl^-$ ions become predominant, so that the difference between the transport numbers of the cartons and anions become larger. The result is that a larger amount of the liquid potential difference is produced between the internal liquid and the liquid under examination such that the electrical potential is fluctuated by changes in the ionic concentration etc. of the liquid under examination.

Such internal liquid is not desirable as an internal liquid for the reference electrode.

For maintaining the function of the internal liquid as a liquid bridge for a prolonged period of time, it is preferred that the internal liquid be in the gellated state or be present in the state of being impregnated with a highly water-absorbent resin. There is no limitation to the method for gellation and any of known gellating techniques may be employed. If a gellating agent, such as agar, is used, it is added in an amount preferably of an order of 3 wt % based on the weight of the internal liquid. It is noted that any of known highly water-absorbent resins, capable of being impregnated with the internal liquid, such as those shown in JP Patent KOKAI Publication No. 62-47546 (1987), may be employed.

In the following preferred embodiments of the present invention will be described in more detail with reference to the appended drawings.

Figure 1:
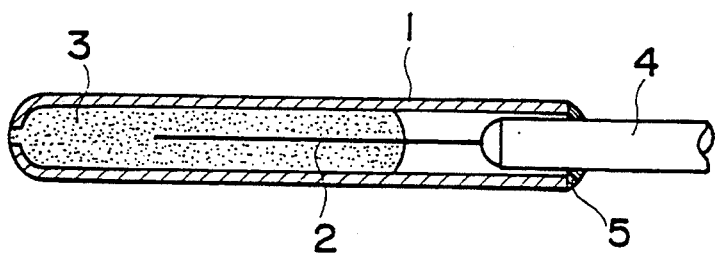
FIG. 1 is a cross-sectional view showing as an embodiment of a reference electrode according to the present invention.

EXAMPLE 1 liter of an aqueous solution containing 0.5 mol of LiCl and 3 mol of $NH_4NO_3$ was prepared and admixed with AgCl powders until saturation of AgCl. The reagents employed were all of an extra class. To the resulting aqueous solution, agar powders (first-class reagent) were added in an amount of 3 wt % and the resulting mass was heated and dissolved under agitation. Before the resulting solution (internal liquid 3) was solidified to form a gel, it was introduced into a glass tube 1 shown in FIG. 1. An Ag/AgCl wire 2 was inserted into the solution in the tube 1 so that the Ag/AgCl wire 2 and the internal liquid 3, now in the gellated state, were intimately contacted with each other. A lead wire 4 and the glass tube 1 were bonded to each other with an epoxy resin 5 to produce a reference electrode. When the reference electrode thus prepared was allowed to stand at room temperature for a prolonged period of time, at least one month, moisture in the agar gel was not vaporized, i.e., the gel was not dried up.

On the contrary, with a comparison electrode which was prepared as conventionally by using a saturated KCl-saturated AgCl solution as a gellated internal liquid and otherwise in the same way as above, and was allowed to stand at room temperature, the gel was dried up in only a few days.

Figure 2:
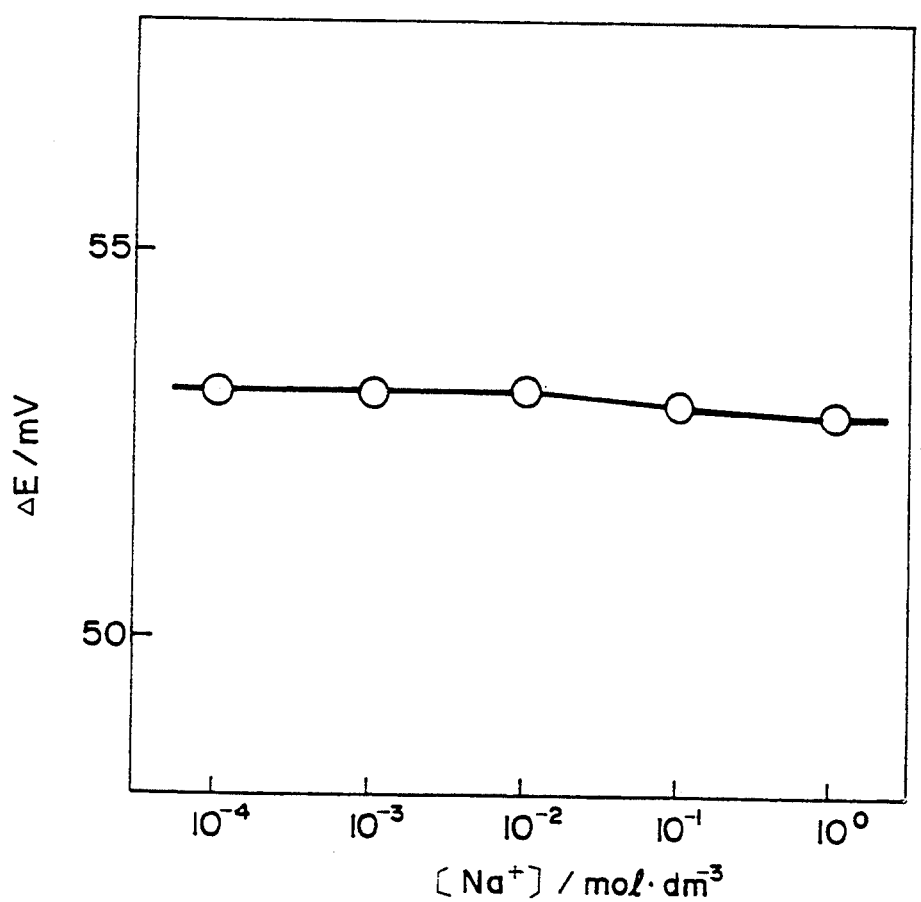
FIG. 2 is a graph showing the relation between the $Na^+$ ion concentration and the electrical potential as obtained in a measurement test with the reference electrode of FIG. 1 connected to a commercial comparison electrode.
Figure 3:
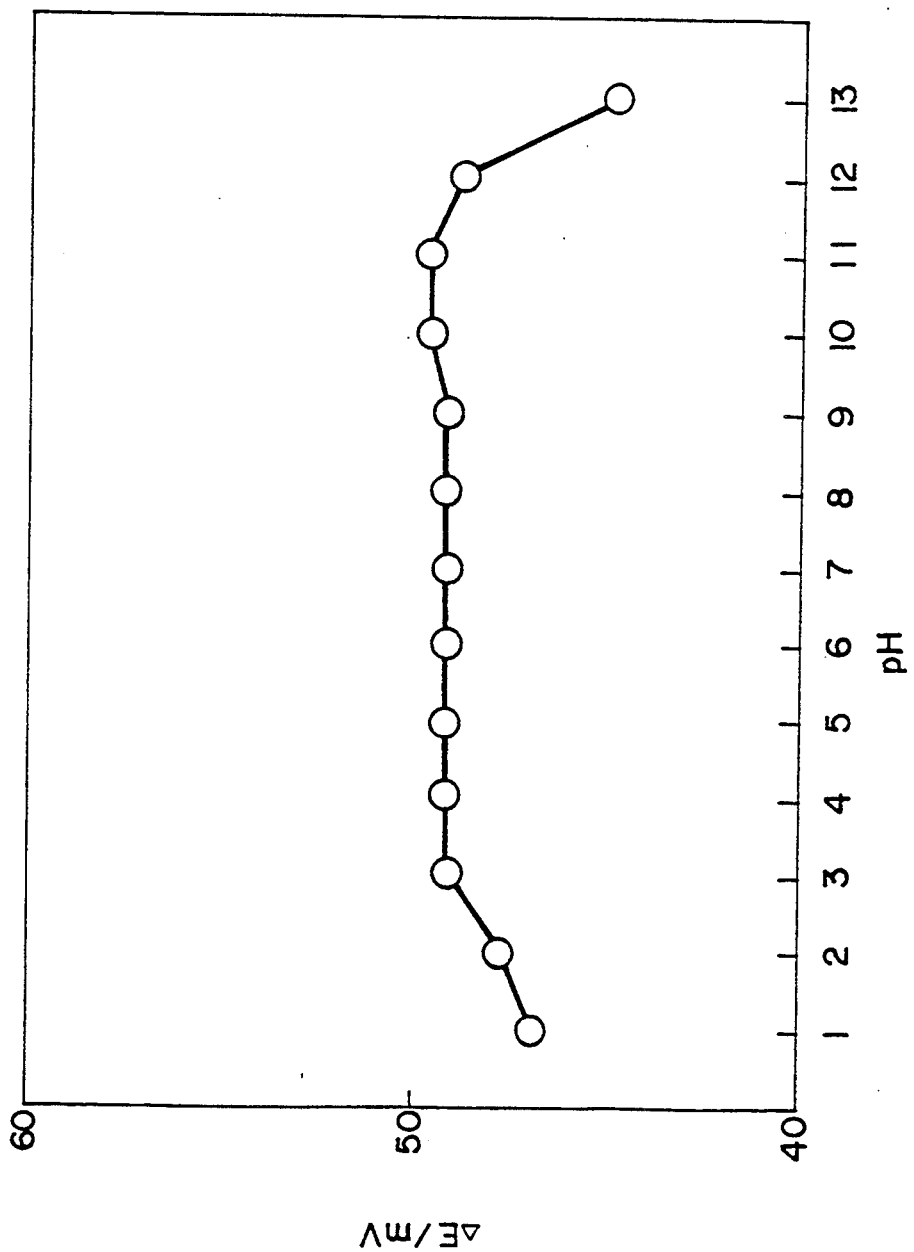
FIG. 3 is a graph similar to FIG. 2 and showing the relation between the pH and the electrical potential.

The potential of the reference electrode of the present Example was measured with respect to that of a commercial reference electrode "HS-205c" manufactured by TOA DEMPA KOGYO KK. It was found that the reference electrode of the present Example showed a substantially constant electrical potential against changes in the sodium ion concentration, as shown in FIG. 2. The reference electrode of the present Example also showed a substantially constant electrical potential against changes in pH in a range of 3 to 12, as shown in FIG. 3.

Although the internal liquid, containing LiCl and $NH_4NO_3$ at these predetermined concentrations, is used in the above Example in connection with the control electrode itself, such internal liquid may obviously be used as an inernal liquid for an ion-selective electrode. Thus the internal liquid, exhibiting this constant electrical potential and which is not dried up for a prolonged period of time, above all, the internal liquid in the gellated state, may also be used effectively as an internal liquid for the ion-selective electrode, if an ion-sensitive material sensitive to particular ions, that is solid electrolyte ceramics or ionophores, are present on the surface thereof in contact with the liquid under examination.

In the above Example, the internal liquid containing LiCl and $NH_4NO_3$ and also containing AgCl to saturation is used for positively inhibiting dissolution through complexing of the electrode ingredient AgCl, such addition of AgCl is merely for assurance sake and may be dispensed with. It is because the concentration of the chloride salt (LiCl) may be lower in the internal liquid of the present invention than in the case of the conventional KCl-containing internal liquid, so that there is scarcely any risk of dissolution of the electrode ingredient AgCl in the form of complexes.

It should be understood that modifications obvious in the art may be done without departing from the gist and scope of the present invention as herein disclosed and claimed in the appended claims.

What is claimed is:

1. A reference electrode comprising, as an internal liquid, LiCl and $NH_4NO_3$ in a dissolved state at a concentration ratio of $[NH_4NO_3]/[LiCl] \geq 4$.

2. The reference electrode as defined in claim 1 wherein the concentration ratio $[NH_4NO_3]/[LiCl]$ is 4 to 8.

3. The reference electrode as defined in claim 2 wherein the LiCl is present in a concentration of $0.1 \text{ mol} \cdot \text{dm}^{-3} \leq [LiCl] \leq 1 \text{ mol} \cdot \text{dm}^{-3}$.

4. The reference electrode as defined in claim 3 wherein the $NH_4NO_3$ is present at a concentration of $[NH_4NO_3] \leq 4 \text{ mol} \cdot \text{dm}^{-3}$.

5. The reference electrode as defined in claim 1 wherein the internal liquid is present in a gellated state.

6. The reference electrode as defined in claim 1 wherein the internal liquid is present as impregnated in a highly water-absorbing synthetic resin.

7. The reference electrode as defined in claim 1 wherein said internal liquid is in contact with a Ag-.AgCl electrode as an internal electrode.

8. An ion-selective electrode comprising an internal reference electrode which is the reference electrode as defined in any one of claims 1 to 7.

9. An internal liquid for a reference electrode comprising LiCl and $NH_4NO_3$ in a dissolved state at an $NH_4NO_3$ to LiCl concentration ratio of $[NH_4NO_3]/[LiCl] \geq 4$.

* * * * *